United States Patent [19]

Bryan

[11] Patent Number: 4,822,456
[45] Date of Patent: Apr. 18, 1989

[54] ION MEASURING APPARATUS AND MONITORING SYSTEM

[76] Inventor: Avron I. Bryan, 26 Country Club Rd., Cocoa Beach, Fla. 32931

[21] Appl. No.: 58,866

[22] Filed: Jun. 5, 1987

[51] Int. Cl.[4] ............................................. G01N 27/30
[52] U.S. Cl. .................................... 204/1 T; 204/412; 204/416; 204/418; 204/419; 204/435
[58] Field of Search ............... 204/412, 416, 418, 419, 204/435, 1 T

[56] References Cited

U.S. PATENT DOCUMENTS

| | | | |
|---|---|---|---|
| 3,862,895 | 1/1975 | King et al. | 204/412 |
| 4,498,039 | 2/1985 | Galwey et al. | 204/412 |
| 4,686,011 | 8/1987 | Jäckle | 204/412 |

Primary Examiner—John F. Niebling
Assistant Examiner—Kathryn Gorgos
Attorney, Agent, or Firm—Macdonald J. Wiggins

[57] ABSTRACT

A real time, on-line ion measurement system for a solution has continuous monitoring of the physical conditions of the ion electrode and the reference electrode of the system. A dual chamber reference electrode is provided having an inner chamber and electrode for providing an ion measurement reference potential, and an outer chamber and electrode for producing a monitoring potential to detect poisoning of the reference electrode membrane. A first time varying low level signal is applied to the ion electrode and a second time varying low level signal orthogonal to and uncorrelated with the first signal is applied to a solution ground electrode disposed in the solution adjacent the reference electrode, the signals producing a composite common ground current. A pair of cross-correlators extracts the two time varying components from the common ground current for measuring the ion electrode and reference electrode impedances. Visual readouts and threshold circuits are provided to indicate when changes in impedances and the reference monitoring potential occur indicative of a system fault.

20 Claims, 2 Drawing Sheets

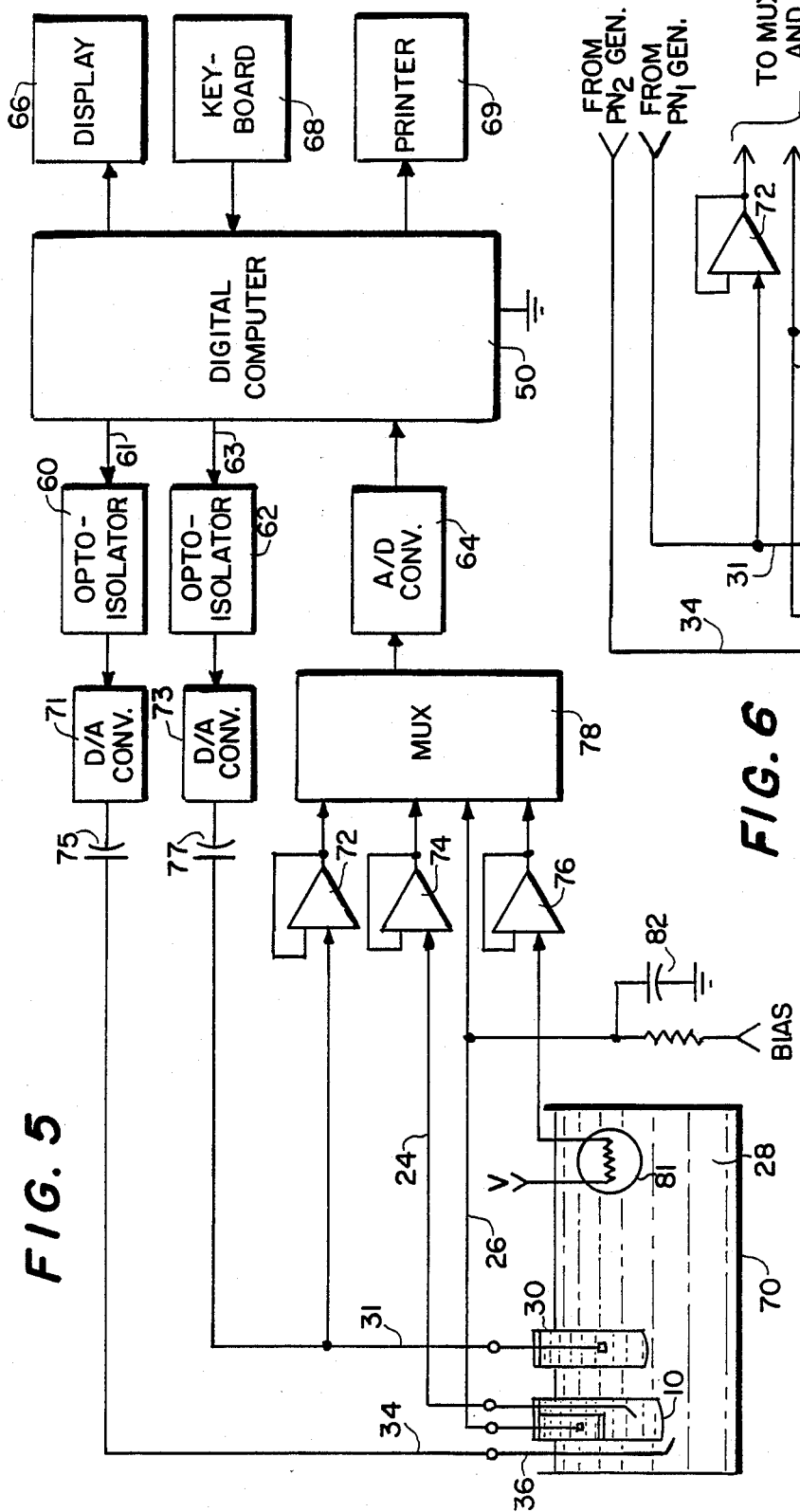
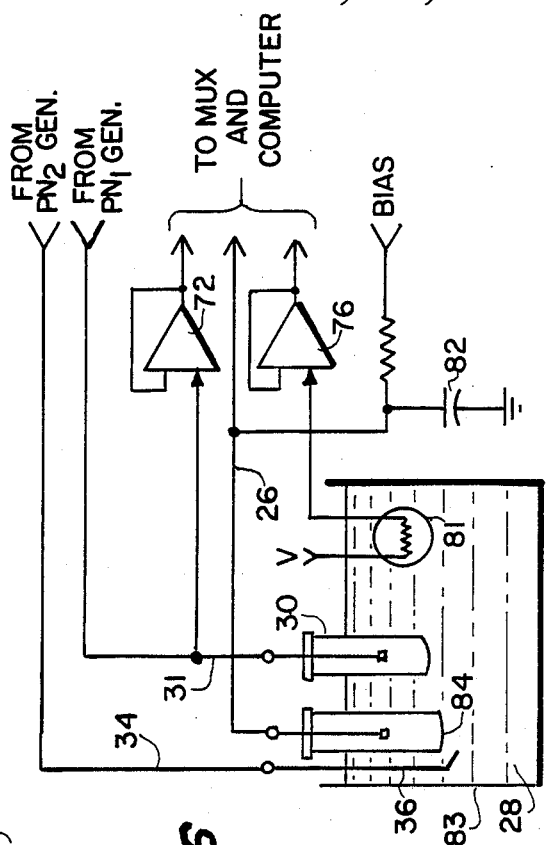
FIG. 5
FIG. 6

ION MEASURING APPARATUS AND MONITORING SYSTEM

BACKGROUND OF THE INVENTION

1. Field of the Invention

The present invention relates to an apparatus for an ion measurement system including means for monitoring the system, and more particularly to apparatus and method for sensing failures in specific ion electrodes and reference electrodes.

2. Description of the Prior Art

The concentration of certain ions is an important parameter in many industrial and medical systems. Measurements of both cations and anions, including sodium, chloride, potassium, nitrate, calcium, ammonia, sulfur dioxide, and hydrogen, may be provided by the use of an ion-selective electrode combined with a reference electrode. The ion electrode and the reference electrode are immersed in a sample of a solution containing the ions of interest and provides a real time direct analytical quantitative measurement of the ion concentration therein. The ion concentration information appears as an electrical potential produced by the ion electrode in combination with the reference electrode operating at a constant potential. Typically, the electrical potential is in the millivolt range. For example, the hydrogen ion measurement system provides a potential of 59.16 mV per decade change of the hydrogen ion activity. In many processes, a continuous measurement is performed, and the process may include alarm systems to indicate when the ion concentration is outside of predetermined limits.

There are a number of problems which can occur with such measurement systems which may result in an undetected failure of the ion electrode or the reference electrode. In many instances, such undetected failures will have catastrophic results. For example, in medical systems, such as kidney dialysis processes, a failure may result in a continuous pH reading of 7.0 while the solution being measured is out of limits. Such failure can and does result in serious damage or death to a patient. In industrial processes, severe economic damages may result from faults, undetected failures, and degradation of ion sensing electrodes such as coating of the electrode by contaminates in the process stream, and physical failure of the electrode such as cracked glass and open leads.

There have been attempts in the prior art to provide means for monitoring ion measurement systems. For example, Blackmer in U.S. Pat. No. 3,661,748 discloses a device in which an ac signal is applied via an electrode to the conductor fluid in which the electrode system is disposed. An ac signal detector is connected to the dc circuitry to measure the ac current flow. A threshold circuit responsive to the output of the ac signal detector indicates fault in the electrochemical sensor system when the output is of a predetermined magnitude. Blackmer utilizes an ac signal level in the 100 millivolt range which is on the same order of magnitude as the dc signals to be measured by the system. In some instances, this large magnitude signal may affect the solution being measured. This system measures a change in resistance of the electrode membrane by a phase detector using the ac signal source as a phase reference. A resistance threshold is provided such that an alarm will sound when the threshold is exceeded. Connery et al, in U.S. Pat. No. 4,189,367, teach a continuous test of an ion selective electrode by sending a dc test current through the electrode system and measuring the voltage change produced. This system measures the total specific ion electrode impedance but does not provide any method of detecting the impedance of the reference electrode or contamination of the reference electrode from the process stream. In the Connery et al system, the procedure periodically applies a dc potential in one polarity and thereafter a second potential in the opposite polarity. A microprocessor analyzes the resulting voltages to determine if any damage has occurred to the ion selective electrode. McAdam et al, U.S. Pat. No. 4,168,220, show a method for detecting the fouling of a membrane cover of an electrical cell by comparing the current output from the cell in its normal mode to the output of a substitute electrode.

None of the above mentioned prior art patents disclose a procedure for monitoring of both the reference cell and the ion selective cell continuously for contamination and for physical failure of the cells. Thus, there is a need for an ion measurement system including a continuous monitoring system which will not affect the measurements but which will show when any change occurs in the measurement system not occasioned by a process change.

SUMMARY OF THE INVENTION

The present invention is an ion measurement system having a real time, on-line system that continuously tests the ion sensing electrode impedance and the reference electrode impedance. The system generates reports on relative changes in the impedance of both electrodes relative to the last calibration of the system. The system detects both coating of the electrode by the process stream contaminants and physical failure of the electrodes.

A preferred embodiment of the ion measuring system of the invention makes use of an improved reference electrode having a double junction construction. The double junction electrode has two separate junctions with two fill solutions which advantageously provides increased chemical separation of the reference junction from the process stream and permits continuous monitoring of the physical integrity of the electrodes. The reference electrode of the invention includes an inner chamber containing an Ag/AgCl electode and a KCl solution. An outside chamber contains a KCl solution and a permeable membrane which forms a liquid junction to the sample. A ceramic plug in the inner chamber provides a liquid junction with the outer chamber. An additional electrode, which may be a platinum wire, is disposed within the outer chamber. Thus, the modified reference electrode has two output leads, one from the inner chamber electrode and one from the outer chamber electrode. As will be discussed more fully below, the outer chamber electrode permits an additional measurement to determine any change between the inner reference electrode potential and the outer reference electrode potential. Such potential measurement between the inner reference electrode and the outer reference electrode will provide information on the integrity of the reference electrode.

When the system is in use, the improved double reference electrode and the ion electrode are disposed in the sample or process stream. An additional sample ground electrode used in monitoring of the system is placed in the sample closely spaced from the reference electrode.

Although it may be possible to operate the system using standard analog measurement techniques, it is preferable to provide a microcomputer with appropriate algorithms to perform all the functions of ion concentration measurement and continuous monitoring of the electrodes. To this end, the dc voltage output from the ion electrode is applied to an analog-to-digital (A/D) converter and the readings therefrom communicated to the microcomputer in binary form. The computer will measure the potentials and convert the digital results to operate analog numerical read-outs of the ion concentration being measured. The outer chamber reference electrode will also produce a dc output voltage which is converted to digital form and interpreted by the microprocessor. This signal will be utilized by appropriate algorithms to determine when a drift in the reference electrode voltage occurs due to poisoning (contamination) of the reference electrode.

It is also desirable to include a temperature sensor in the process stream. The output of the temperature sensor is converted to digital form which is utilized by the microcomputer to compensate the ion concentration readings and the reference and electrode impedances for changes in temperature.

Monitoring of the mechanical integrity of the reference and ion electrodes is provided by a continuous measurement of the impedance through each electrode. To measure these impedances of the reference electrode and the ion electrode, two low level orthogonal test signals, which are preferably pseudorandom binary signals, are applied continuously to the system. Each signal is of a very low level, for example less than 0.2 millivolts, and consequently will not interfere with measurements of the dc voltages produced by the electrodes. A first test signal is applied to the ion electrode, and a second signal is applied to the sample ground electrode. A current from the first pseudorandom test signal will flow via the ion electrode through the sample to the reference electrode, then through the outer chamber and inner chamber and is output at the reference cell terminal. Similarly, a small current from the second pseudo random signal will flow from the solution ground connection through the sample to the reference electrode and out of the reference cell terminal.

As may now be understood, the two pseudorandom currents will be flowing in the reference electrode output along with the dc voltage therefrom and will add and subtract from the dc currents from the cells. The composite signal is converted by the A/D converter and applied to the microcomputer, which is programmed to cross-correlate each pseudorandom current with its source current. This action extracts and separates the two pseudorandom signals from the composite signal. Each extracted signals is then subtracted from the composite signal which provides the computer with the dc potential of the ion electrode. The normal impedance of the ion electrode is greater than 1 megohm while the reference electrode impedance is less than 10K ohms, and the solution impedance between the sample ground electrode and the reference electrode is usually less than 1000 ohms. The magnitude of the ion cell pseudorandom signal is therefore determined almost entirely by the ion electrode impedance while the reference electrode test current magnitude is determined almost entirely by the reference electrode impedance. The magnitudes of the two extracted pseudorandom signal currents will therefore be proportional to the impedances of the respective electrodes and these values will be sensed by the computer.

At the time of calibration of the system, the initial electrode impedances and potentials will be measured and stored, and thereafter the monitored values will be compared therewith. Any large change in either the ion and reference electrode impedances would indicate a possible failure, such as cracked glass, contact failure or coating of the electrodes by the process stream materials. Poisoning of the reference electrode would be detected by potential changes in the outer chamber reference electrode with respect to the inner chamber electrode.

There are certain capacitances involved in the electrodes and the solutions; therefore, the pseudorandom signals are produced at a low bit rate such as 1 bit per second to eliminate any effect of these capacitances and the measurements will provide the resistive component of the electrode impedances.

BRIEF DESCRIPTION OF THE DRAWINGS

FIG. 5 is a block diagram of the preferred system of the invention utilizing a microcomputer; and FIG. 6 is a simplified schematic diagram of an alternative embodiment of the invention.

DETAILED DESCRIPTION OF THE PREFERRED EMBODIMENT

Figure 1:
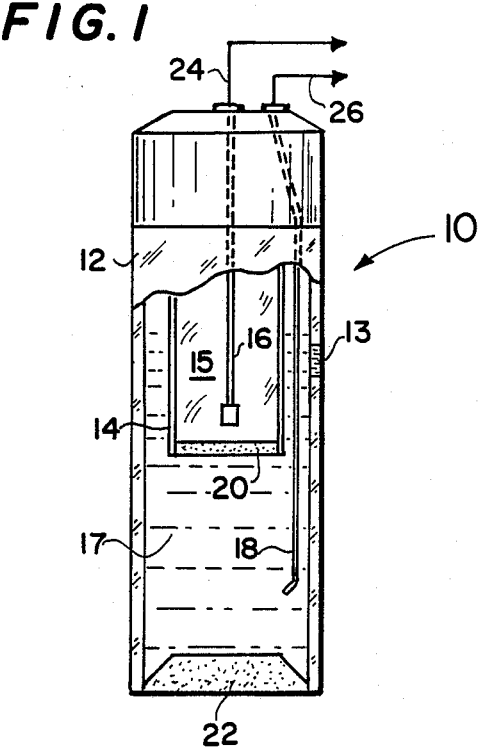
FIG. 1 is a partially cut away view of a double chamber reference electrode cell in accordance with the invention.

The invention involves a specific ion electrode and a reference electrode in a system for measuring the concentration of a specific ion in a process stream or sample solution and having means for monitoring the integrity of the reference and ion electrodes. Although the monitoring portion of the system will work with existing single chamber reference electrodes, it is preferred to utilize a double chamber reference cell shown in partial cut away view in FIG. 1. The reference electrode 10 has an outer glass envelope 12 having a permeable junction 22 which will be immersed in the sample or process stream. An outer chamber or bridge electrode 18, which may be a platinum wire or the like, is disposed in the outer chamber and has an output lead 26. A filling hole 13 is provided and the outer chamber is filled with a suitable electrolyte solution such as a saturated solution of potassium chloride (KCl). Electrode 18 may be a silver wire coated with silver chloride (AgCl) or a platinum wire coated with calomel ($Hg_2Cl_2$). An inner chamber 14 includes a permeable plug 20 which may be ceramic, quartz fiber, or plastic as is well known in the art. A reference electrode 16 of similar construction to outer chamber electrode 18 is disposed in inner chamber 14 and includes an output lead 24 therefrom. Inner chamber 14 is filled with an electrolyte such as KCl.

Figure 2:
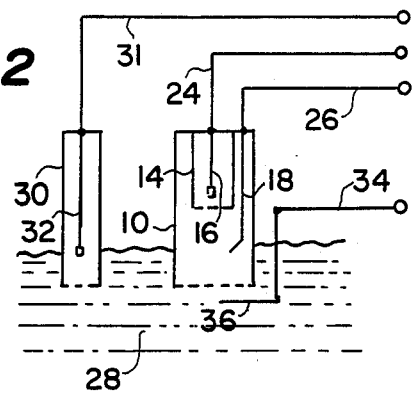
FIG. 2 is a schematic diagram of a measuring system in accordance with the invention for measuring ion concentration using the double chamber reference electrode cell of FIG. 1.

FIG. 2 shows a schematic diagram of the double junction reference electrode 10 and a specific ion electrode 30 immersed in a solution 28 for which the ion concentration is to be measured. In accordance with the invention, a solution ground electrode 36 is also disposed in solution 28 a short distance from reference cell 10. For example, the separation may be on the order of 0.1 inches from the reference electrode.

The specific ion electrode 30 has an ion electrode 32 having an output lead 31 therefrom. Solution ground electrode 36 has a lead 34 therefrom.

Figure 3:
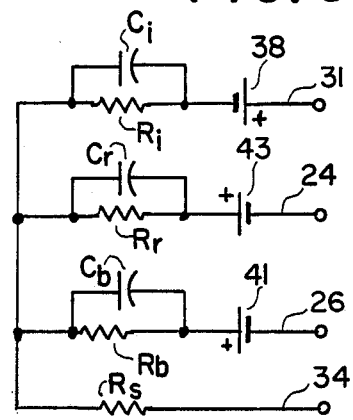
FIG. 3 is an equivalent electrical circuit for the system of FIG. 2.

Turning now to FIG. 3, a simplified equivalent electrical circuit of the system of FIG. 2 is shown. Lead 31, which connects to the ion electrode 32 of FIG. 2, will have a small potential created thereon by the electrode 32 and the cell solution indicated by battery 38. As is well known in the art, ions from solution 28 will cause the voltage of cell 38 to vary in accordance with the concentration of such ions. The path from the electrode 32 to reference electrode 10 is through the glass envelope of ion electrode 30 and is represented in FIG. 3 by a resistance $R_i$ and a parallel capacitance $C_i$. The impedance of the path is very high and is generally greater than 1 megohm. The inner chamber electrode 16 of reference electrode 10 forms a voltage source 43 as a function of the electrolyte and the electrode 16 material. In accordance with known ion measuring systems, this potential is required to be constant and serves as a half cell reference for the half cell ion electrode 30. As will be shown hereinbelow, a bias may be placed on lead 24. The electrical path from inner chamber electrode 16 through the outer chamber and permeable membrane of reference cell 10 is represented in FIG. 3 by a resistance $R_r$ in parallel with the capacitance $C_r$. Generally, $R_r$ will have a relatively low resistance on the order of 10,000 ohms. Outer chamber electrode 18 of reference cell 10 also forms a voltage source 41 in conjunction with the electrolyte therein and will have an impedance through the permeable membrane to the solution in which the resistive component $R_b$ is somewhat less than $R_r$, and parallel with capacitance $C_b$. The current path from solution ground electrode 36 to reference electrode 10 will be essentially resistive and will have a resistance $R_s$ on the order of 1000 ohms for most samples.

Figure 4:
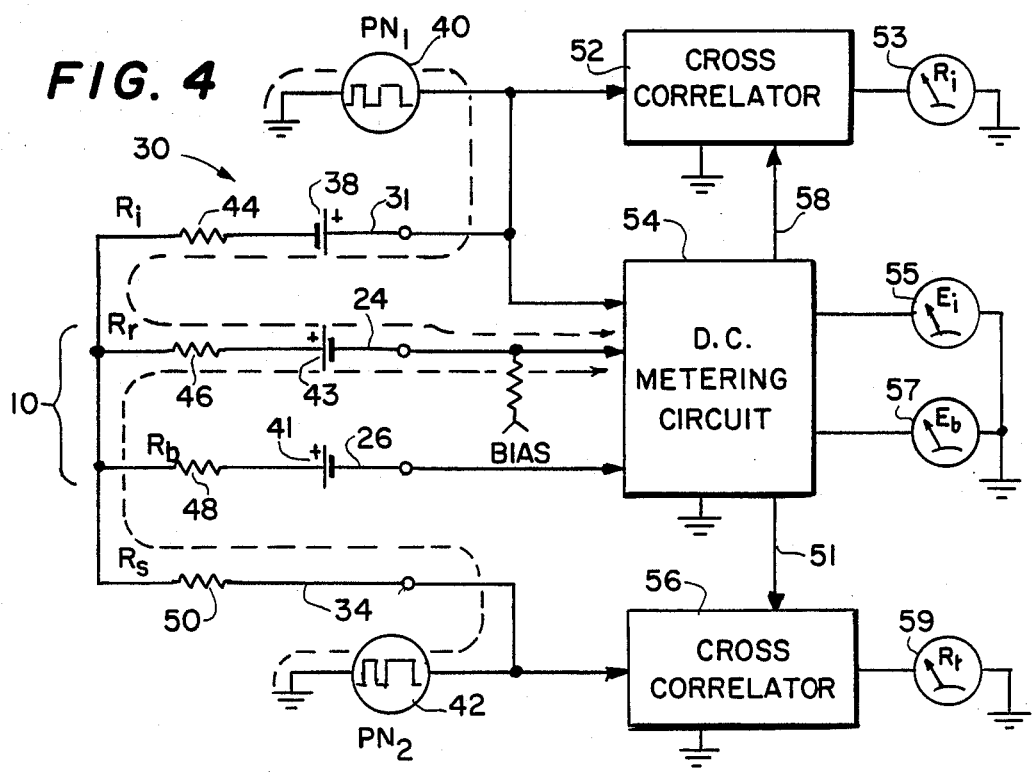
FIG. 4 is a simplified schematic diagram of an ion measuring system in accordance with the invention.

Having described the equivalent circuit of a typical installation, the schematic block diagram of FIG. 4 will be utilized to explain the operation of the invention. A dc metering circuit 54 is provided having an input from lead 31 of ion electrode 30. Dc metering circuit 54 also includes an input from lead 24 of reference electrode 10 and an input from lead 26 from the outer chamber of bridge electrode of the reference cell. Lead 24 from the inner cell reference electrode is connected to a source of bias.

Dc metering circuit 54 serves to combine the dc inputs from the three electrolytic cells and to produce an output voltage $E_i$ for operating meter 55. This voltage will represent the ion concentration of the sample or process stream. As will be understood, this meter reading will vary as the process ion concentration varies. Similarly, dc metering circuit 54 produces an output voltage $E_b$ which is referred to as the bridge potential created at the outer chamber or bridge electrode 18. For a perfect reference cell 10, this voltage will be constant, at least for a specific temperature. Assuming constant temperature, any poisoning of membrane 22 of FIG. 1 due to contaminants from the process stream will affect the normal diffusion through membrane 22 and a drift in the value of $E_b$ will be noted as such fouling or poisoning occurs. Thus, the electrolytic cell provided by the outer chamber of reference electrode 10 will first be affected when any poisoning occurs.

The double construction of electrode 10 performs two functions: it provides a separate electrolytic cell which will give an early indication of a problem long prior to the poisoning of the reference cell in the inner chamber; and it will provide an indication to the operator when such poisoning is just beginning thereby permitting appropriate maintenance. Any material failure such as a crack in glass envelope 12 or in the membrane 22 will cause a sudden step change in the bridge potential which will be noted by an operator.

In addition to this monitoring function, the invention utilizes a means of measuring the effective cell resistances for changes occasioned by mechanical or physical failures and poisoning of the electrodes. To measure any changes in the resistance of the inner chamber membrane 20 in FIG. 1, a low level pseudorandom signal $PN_2$ is produced by generator 42 and applied to lead 34 to the solution ground. Generator 42 thus causes a pseudorandom current $i_2$ to flow through the solution as indicated by the dashed line. The pseudorandom signal generated by generator 42 is preferably a binary signal having a fundamental bit rate on the order of 1 Hz. Therefore, the capacitances shown in FIG. 3 will not affect the current $i_2$. As may now be understood, the value of current $i_2$ flowing through $R_r$ will be almost directly proportional to the value of $R_r$ since $R_s$ is an order of magnitude smaller.

Pseudorandom signal generator 40 generates a second pseudorandom signal $PN_1$ and has its output connected to lead 31 of ion electrode 30 causing a current $i_1$ to flow through the ion cell resistance $R_i$, the reference cell resistance $R_r$, and through dc metering circuit 54 to ground. Thus, a load impedance in dc metering circuit 54 will be carrying the composite signal from $i_1$, $i_2$, and the dc currents flowing from lead 24. It will be noted that pseudorandom generator 42 has its output connected to cross-correlator 56 and pseudorandom signal generator 40 has its output connected to cross-correlator 52. The signals from generators 40 and 42 are orthogonal and, therefore, are uncorrelated. The potential produced across the load in metering circuit 54 is connected to cross-correlators 52 and 56 by leads 58 and 51, respectively. Cross-correlator 52 will therefore provide an output proportional to the pseudorandom current $i_1$ while cross-correlator 56 will produce an output proportional to the pseudorandom current $i_2$. An output from cross-correlator 52 will operate metering circuit 53 which is calibrated to read the resistance $R_i$ and the output from cross-correlator 56 will operate meter 59 calibrated to read $i_2$.

When the ion measuring system is operating normally, $R_i$ and $R_r$ will remain constant. If the ion electrode 30 becomes contaminated or coated resulting in an increase in the resistance $R_i$ then this change will be noted on meter 53. If a lead or connection should break producing an open circuit for $R_i$, this would also be indicated by meter 53. If the glass should crack or similar defect should occur, then the value of $R_i$ indicated by meter 53 would drop. Similarly, meter 59 will monitor the condition of the inner chamber of reference electrode 10.

Although pseudorandom binary signals are preferred for measurement of $R_r$ and $R_i$, any pair of orthogonal, non-correlated test signals may be used.

Having described the theory of operation with reference to the exemplary version of FIG. 4, a preferred system utilizing a microcomputer will be described with reference to FIG. 5.

A process solution 28 for which the ion concentration is to be measured is shown in a tank 70. The reference electrode 10 of the invention and a specific ion electrode 30 are shown immersed in process 28. In addition, a temperature sensor 81, which may be a resistance type or other electrical temperature sensor, is provided to permit automatic compensation for variations in process solution temperature. A microcomputer 50 is provided having a number of stored programs. One program is utilized to generate first and second pseudorandom signals. As previously discussed, it is desirable that the pseudorandom signals be of a binary nature and at a relatively low frequency such as one bit per second. The two pseudorandom signals are uncorrelated with each other. A first pseudorandom signal is produced by microcomputer 50 on lead 63 and fed to digital-to-analog (D/A) converter 73 via optoisolator 62. A blocking capacitor 77 is utilized to remove any dc component in the pseudorandom signal. The first pseudorandom signal is connected to lead 31 of ion electrode 30. Similarly, the second pseudorandom signal appears on lead 61 from microcomputer 50 and is coupled to the D/A converter 71 via optoisolator 60 and the dc component removed by blocking capacitor 75.

The dc cell outputs from bridge electrode lead 24 and ion electrode lead 31 are connected via emitter followers 74 and 72, respectively, to multiplexer (MUX) 78. The potential on reference electrode lead 26 is connected directly to MUX 78 and to a source of bias with capacitor 82 providing an ac ground therefor. Temperature sensor 81 has its output connected to MUX 78 via an emitter follower 76. Multiplexer 78 has its output connected via analog-to-digital converter 64 to microcomputer 50. As previously discussed, the voltage level of the pseudorandom signals applied to the electrodes may be on the order of 0.2 millivolts or less while the biased dc signals are in the hundreds of millivolts range. Therefore, A/D converter 64 necessarily has high resolution capability. Microcomputer 50 is programmed to provide the necessary cross-correlation operation with respect to the pseudorandom signals and to extract the values of $R_i$ and $R_r$ therefrom. These resistance values are then displayed on display 66. Microcomputer 50 may also have thresholds selected which will produce alarm signals when the thresholds are exceeded. The value of the ion concentration and the potential $E_b$ of the outer chamber electrode are also extracted from the composite signals and the values may be displayed on display 66. If desired, any information in microcomputer 50 may be printed out on printer 69.

Calibration of the system may be carried out by entering appropriate keyboard commands via keyboard 68. The microcomputer is programmed to reset the thresholds at calibration.

ALTERNATIVE EMBODIMENT

In the embodiment described hereinabove, a double reference junction electrode has been used to provide additional isolation of the reference junction from the process stream and to permit the use of a outer chamber electrode for an additional potential measurement. However, in an alternative embodiment of the invention shown in schematic form in FIG. 6, the measuring and monitoring portion of the invention may be used with a single reference junction electrode 74 and the solution ground electrode 36. A solution 28 involved in the process to be measured is shown disposed in a tank or container 84. The reference electrode 84 and ion electrode 30 are immersed in solution 31 and solution ground electrode 36 is disposed closely spaced from reference electrode 84 as previously discussed. A temperature sensor 81 may also be utilized to permit compensation for variations in process temperature.

Solution ground electrode 36 is connected to a first source of pseudorandom current from a suitable source which may be computer 50 as shown in FIG. 5. Ion electrode 30 is driven by a second pseudorandom source which is orthogonal and uncorrelated with the signal from the first source connected to solution ground 36.

A first pseudorandom current will flow through ion electrode to reference electrode 84 and the computer (such as computer 50 arranged as indicated in FIG. 5) via lead 26. A second uncorrelated pseudorandom current will flow via lead 34 in ground electrode 36 to the reference electrode and to the computer 50 on lead 26. As previously described, a computer, such as computer 50 in FIG. 5, is programmed to cross-correlate each of the pseudorandom signals with its respective source signal to thereby separate each signal from the composite signal on lead 26. Readouts of reference electrode membrane resistance and ion electrode glass resistance are obtained as previously described and may be utilized in conjunction with thresholds to produce alarms when the thresholds are exceeded. The dc ion concentration signals are also separated and displayed.

As will now be recognized, an apparatus has been disclosed for a system which provides measurements of ion concentration in a sample or process stream, and which includes means for measurement of the resistance through the reference electrode and resistance through the ion electrode. The system thereby provides a warning when such resistances vary from calibrated values, and in which slow variations in resistance indicate poisoning or coating of the electrodes by contaminants in the process stream and abrupt changes indicate breakage or similar failures.

As will be recognized, the apparatus involves the method steps of:

a. providing a reference electrode having an outer chamber and an inner chamber;

b. connecting an electrode in the inner chamber to a source of bias and connecting an electrode in the outer chamber to a resistance measurement circuit;

c. disposing a solution ground electrode immediately adjacent the double reference electrode;

d. driving the solution ground electrode from a first pseudorandom signal source;

e. providing an ion electrode immersed in the process stream;

f. connecting the ion electrode to an ion concentration measurement circuit;

g. driving the ion electrode from a second pseudorandom signal source in which the second signal is uncorrelated and orthogonal to the first signal;

h. connecting the ion electrode to a resistance measuring circuit;

i. separating the first resistance measurement signal from the second resistance measurement signal and the dc ion concentration measurement signal by cross-correlation of the first pseudorandom signal with its source signal; and j. separating the second pseudorandom signal by crosscorrelating the signal with its source signal.

I claim:

1. In an on-line, real time ion measurement system having an ion electrode and a reference electrode immersed in a solution to be measured, a device for continuous monitoring of the impedances of said ion electrode and said reference electrode comprising:

a solution ground electrode immersed in said solution and closely spaced from said reference electrode;

first signal producing means for producing a first time varying electrical signal, said first signal applied across said ion electrode and a common ground, thereby producing a first time varying ground current proportional to the impedance of said ion electrode;

second signal producing means for producing a second time varying electrical signal orthogonal and uncorrelated with said first signal, said second signal applied across said solution ground electrode and said common ground, thereby producing a second time varying ground current proportional to the impedance of said reference electrode;

first cross correlator means having a first input connected to said first signal producing means and a second input connected to receive a signal proportional to said first time varying ground current, said first cross correlator means for producing an output proportional to the magnitude of said first time varying ground current indicative of the impedance of said ion electrode; and second cross correlator means having a first input connected to said second signal producing means and a second input connected to receive a signal proportional to said first time varying ground current, said second cross correlator means for producing an output proportional to the magnitude of said second time varying ground current indicative of the impedance of said reference electrode.

2. The system as recited in claim 1 which further comprises:

first readout means connected to said first cross correlator means output for indicating said ion electrode impedance; and second readout means connected to said second cross means correlator output for indicating said reference electrode impedance.

3. The system as recited in claim 2 in which said first and second readout means include alarm means for producing an alarm when either of said impedance values differ from a preselected value range.

4. The system as recited in claim 1 in which first and second signal producing means each produce a pseudorandom binary signal.

5. The system as recited in claim 1 further comprises:
means for measuring a dc component of said common ground current proportional to an ion concentration value for said solution; and
means for indicating said ion concentration value.

6. The system as recited in claim 5 in which said first and second time varying signals are at least an order of magnitude less amplitude than said decomponent of said common ground current.

7. The system as recited in claim 4 in which said first and second cross correlators include computer means for receiving said first and second time varying ground current signals, for digitizing said ground current signals, for receiving said pseudorandom binary signals, and for producing said first and second outputs.

8. In a system for continuous measurement of the ion concentration of a solution having an ion electrode and a reference electrode each immersed in said solution, apparatus for monitoring said ion electrode and said reference electrode for changes in characteristics thereof comprising:

a solution ground electrode immersed in said solution and closely spaced from said reference electrode;

first means for producing a first time varying electrical signal, said first signal applied across said ion electrode and a common ground, thereby producing a first component of a common ground current;

second means for producing a second time varying electrical signal orthogonal and uncorrelated with said first signal, said second signal applied across said solution ground electrode and said common ground, thereby producing a second component of a common ground current;

a first correlator having a first input connected to said first signal producing means and a second input connected to receive a signal proportional to said common ground current, said first correlator producing an output proportional to the magnitude of said first component of said common ground current indicative of the impedance of said ion electrode; and a second correlator having a first input connected to said second signal producing means and a second input connected to receive said signal proportional to said common ground current, said second correlator producing an output proportional to the magnitude of said second component of said common ground current indicative of the impedance of said reference electrode.

9. An ion measurement system having an ion electrode and an electrode monitoring system comprising:

a. a reference electrode cell for providing a reference voltage to said ion measurement system, said cell having
   i. an outer nonconductive envelope,
   ii. a first permeable junction membrane closing a first end of said outer envelope thereby forming an outer chamber,
   iii. an inner nonconductive envelope disposed within said outer envelope,
   iv. a second permeable junction membrane closing a first end of said inner envelope thereby forming an inner chamber,
   v. a first electrode element disposed in said outer chamber,
   vi. a second electrode element disposed in said inner chamber,
   vii. a first electrolyte filling said first chamber, and
   viii. a second electrolyte filling said second chamber, said reference electrode cell immersed in a solution to be measured;

b. a solution ground electrode immersed in said solution and closely spaced from said reference electrode cell;

c. means connected to said second electrode element for providing a dc reference voltage to said measurement system with respect to a common ground, said means producing a fixed dc component of a common ground current;

d. means for producing a time varying electrical signal, said signal applied across said solution ground electrode and said common ground, thereby producing a time varying component of said common ground current;
e. a cross correlator having a first input connected to said signal producing means and a second input connected to receive a signal proportional to said common ground current, said cross correlator producing an output proportional to the magnitude of said time varying component of said common ground current indicative of the impedance of said reference electrode cell; and
f. a dc measurement circuit connected to said first electrode for monitoring a normally constant voltage from said first electrode element indicative of the physical condition of said reference electrode cell.

10. A real time, on-line system for measurement of ion concentration in a solution having monitoring of ion electrodes and reference electrodes of the system comprising:
a. an ion electrode immersed in said solution for producing an ion potential proportional to an ion concentration of said solution;
b. a reference electrode cell for immersion in said solution, and having an inner chamber and an outer chamber, said inner chamber separated from said outer chamber by a first permeable membrane, and said outer chamber separated from said solution by a second permeable membrane, said inner and outer chambers filled with respective electrolytes;
c. a reference electrode element disposed in said inner chamber of said reference electrode cell;
d. a monitoring electrode element disposed in said outer chamber of said reference electrode cell;
e. a solution ground electrode immersed in said solution and closely spaced from said reference electrode cell;
f. first means for producing a first time varying electrical signal, said first signal applied across said ion electrode and a common ground, thereby producing a first time varying component of a common ground current;
g. second means for producing a second time varying electrical signal orthogonal and uncorrelated with said first signal, said second signal applied across said solution ground and said common ground, thereby producing a second time varying component of said common ground current;
h. a dc measurement circuit connected to said monitoring electrode element for monitoring a normally constant voltage from said monitoring electrode element indicative of the physical condition of said reference electrode cell;
i. a first cross correlator having a first input connected to said first signal producing means and a second input connected to receive a signal proportional to said common ground current, said first cross correlator producing a first output proportional to the magnitude of said first time varying component of said common ground current indicative of the impedance of said ion electrode; and
j. a second cross correlator having a first input connected to said second first signal producing means and a second input connected to receive said signal proportional to said common ground current, said second cross correlator producing a second output proportional to the magnitude of said second time varying component of said common ground currents indicative of said reference electrode cell impedance.

11. A real time, on-line system for measurement of ion concentration in a solution having monitoring of the physical conditions of an ion electrode and a reference electrode of the system comprising:
a. an ion electrode immersed in said solution for producing an ion potential proportional to an ion concentration of said solution;
b. a reference electrode cell immersed in said solution for producing a reference potential, said cell having an inner chamber and an outer chamber, said inner chamber separated from said outer chamber by a first permeable membrane, and said outer chamber separated from said solution by a second permeable membrane, said inner and outer chambers filled with respective electrolytes;
c. a reference electrode element disposed in said outer chamber of said reference electrode cell;
d. a monitoring electrode element disposed in said outer chamber of said reference electrode cell;
e. a solution ground electrode immersed in said solution and closely spaced from said reference electrode; and
f. a digital computer having a programmable memory, a temporary memory, and a display, said computer programmed to
  i. generate a first pseudorandom binary signal, said computer having a first output for communicating said first signal to said ion electrode,
  ii. generate a second pseudorandom binary signal orthogonal and uncorrelated with said first signal, said computer having a second output for communicating said second signal to said solution ground,
  iii. cross correlate a signal proportional to a common ground current signal from said reference electrode cell to said computer, said computer having a first input connected to said reference electrode, said cross correlation producing a first display output to said display indicative of the impedance of said reference electrode cell,
  iv. cross correlate a signal proportional to said common ground current signal from said ion electrode to said computer via said first input thereto, said cross correlation producing a second output to said display indicative of the impedance of said ion electrode,
  v. monitor, via a second input, said reference electrode cell impedance and said ion electrode impedance for comparison with values calculated and stored in said temporary memory, and
  vi. display said ion and reference electrode cell impedances, said computer including a third input connected to said ion electrode and programmed to measure and display an ion concentration therefrom.

12. The system as recited in claim 11 in which said computer is further programmed to produce an alarm when said ion electrode impedance or said reference electrode cell impedance is not within a preprogrammed value range.

13. The system as recited in claim 11 in which said computer is further programmed to monitor a fixed dc voltage from said monitoring electrode and to display said voltage.

14. The system as recited in claim 13 in which said computer is further programmed to produce an alarm when said voltage varies from a preprogrammed fixed value.

15. The system as recited in claim 14 in which said computer is programmed to measure and display an ion concentration indicated by a dc ion voltage from said ion electrode.

16. The system as recited in claim 11 in which said computer includes analog-to-digital converter means for digitizing analog signals from said first, second and third inputs.

17. The system as recited in claim 11 in which said computer includes:
   a multiplexer having inputs connected to said first, second and third inputs; and
   an analog-to-digital converter having an input connected to an output of said multiplexer and an output connected to a fourth input of said computer.

18. The method of monitoring the physical condition of a reference electrode and an ion electrode in a system having a reference electrode cell and an ion electrode for continuous measurement of an ion concentration of a solution where the method comprises:
   a. disposing a solution ground electrode adjacent the reference electrode cell;
   b. driving the solution ground electrode against a common ground with a first time varying signal from a first source thereby producing a first signal component of a common ground current;
   c. driving the ion electrode against the common ground with a second time varying signal from a second source in which the second signal is uncorrelated and orthogonal to the first signal thereby producing a second signal component of the common ground current;
   d. cross-correlating the common ground current with said first time varying signal to produce a first output proportional to the impedance of the reference electrode cell; and
   e. cross-correlating the common ground current with said second time varying signal to produce a second output proportional to the impedance of the ion electrode.

19. The method as recited in claim 18 including the further steps of:
   f. providing a measuring circuit having first and second threshold impedance ranges;
   g. comparing the first output to the first threshold range and producing an indication when the ion electrode impedance differs from the first threshold range; and
   h. comparing the second output to the second threshold range and producing an indication when the reference electrode impedance differs from the second threshold range.

20. The method as recited in claim 18 including the further steps of:
   f. providing a second chamber in the reference electrode cell between a reference electrode in the cell and the solution;
   g. providing a monitoring electrode in the second chamber of the reference electrode cell;
   h. measuring a potential from the monitoring electrode; and
   i. establishing a potential threshold range for the monitoring electrode and comparing the monitoring electrode potential with the threshold range for producing an indication when such monitoring electrode potential differs from the threshold range.

* * * * *